United States Patent [19]

Sakai et al.

[11] 3,996,263
[45] Dec. 7, 1976

[54] 9-OXO-11α-METHYL-15 ξ-HYROXY-PROST-13(TRANS)-ENOIC ACID DERIVATIVES AND PROCESS FOR THE PREPARAION THEREOF

[75] Inventors: Kiyoshi Sakai; Takashi Yusa; Junya Ide; Mitsuo Yamazaki; Shinsaku Kobayashi, all of Tokyo, Japan

[73] Assignee: Sankyo Company Limited, Tokyo, Japan

[22] Filed: May 5, 1975

[21] Appl. No.: 574,376

[52] U.S. Cl. .................. 260/468 D; 260/310.9; 260/343.3 R; 260/410.9 R; 260/413; 260/468 K; 260/514 K; 260/514 D; 424/305; 424/317
[51] Int. Cl.² .................................. C07C 177/00
[58] Field of Search ............... 260/468 D, 514 D

[56] References Cited
UNITED STATES PATENTS

| 3,849,474 | 11/1974 | Abraham et al. | 260/408 |
| 3,899,525 | 8/1975 | Oda et al. | 260/463 |

FOREIGN PATENTS OR APPLICATIONS

| 2,437,622 | 2/1975 | Germany | 260/468 |

OTHER PUBLICATIONS

B491,711, Mar. 1976, Kao et al., 260/240 R.

*Primary Examiner*—Robert Gerstl
*Attorney, Agent, or Firm*—Flynn & Frishauf

[57] ABSTRACT

Prostanoic acid derivatives having the formula

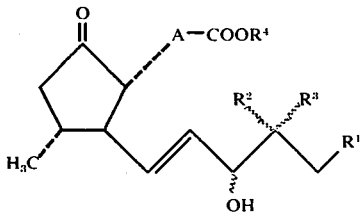

wherein A represents an alkylene group having from 4 to 8 carbon atoms, $R^1$ represents an alkyl group having from one to 5 carbon atoms, $R^2$ and $R^3$ may be the same or different and each represents hydrogen atom or an alkyl group having from one to 4 carbon atoms and $R^4$ represents hydrogen atom or an alkyl group having from one to 4 carbon atoms and the pharmaceutically acceptable salts thereof and also relates to a process for the preparation thereof.

The compounds are useful as anti-ulcerogenic agents and may be prepared by reducing a compound having the formula

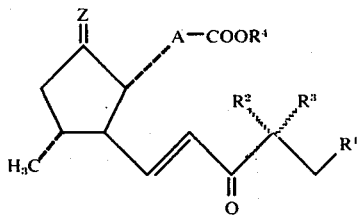

wherein A, $R^1$, $R^2$, $R^3$ and $R^4$ are the same above and Z represents a carbonyl-protecting group to give a compound having the formula

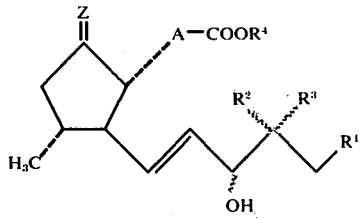

wherein A, $R^1$, $R^2$, $R^3$, $R^4$ and Z are the same as above and removing the carbonyl-protecting group from the latter compound.

4 Claims, No Drawings

9-OXO-11α-METHYL-15-ξ-HYDROXYPROST-13(TRANS)-ENOIC ACID DERIVATIVES AND PROCESS FOR THE PREPARAION THEREOF

This invention relates to novel prostaglandin derivatives and a novel process for the preparation thereof.

More particularly, it relates to prostaglandin derivatives having the formula

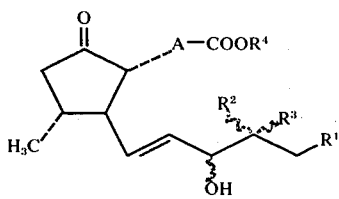

(I)

wherein A represents an alkylene group having from 4 to 8 carbon atoms, $R^1$ represents an alkyl group having from one to 5 carbon atoms, $R^2$ and $R^3$ may be the same or different and each represents hydrogen atom or an alkyl group having from one to 4 carbon atoms and $R^4$ represents hydrogen atom or an alkyl group having from one to 4 carbon atoms and the pharmaceutically acceptable salts thereof and also relates to a process for the preparation thereof. The prostaglandin derivatives (I) have utility as anti-ulcerogenic agents.

In the above formula (I), A may be a straight or branched alkylene group having from 4 to 8 carbon atoms, preferably, tetramethylene, pentamethylene, 1-methylpentamethylene, 2-methylpentamethylene, hexamethylene, 1-methylhexamethylene, 2-methylhexamethylene, heptamethylene, 1-methylheptamethylene and octamethylene. $R^1$ may be a straight or branched alkyl group having from one to 5 carbon atoms, preferably, methyl, ethyl, n-propyl, isopropyl, n-butyl, isobutyl, n-pentyl and isopentyl, $R^2$ and $R^3$ may be the same or different and each may be hydrogen atom or a straight or branched alkyl group having from one to 4 carbon atoms, preferably, methyl, ethyl, n-propyl, isopropyl, n-butyl and isobutyl. $R^4$ may be hydrogen atom or a straight or branched alkyl group having from one to 4 carbon atoms, preferably, methyl, ethyl, n-propyl, isopropyl, n-butyl and isobutyl.

A preferred group of the prostaglandin derivatives provided by the invention is those of the formula (I) wherein A represents hexamethylene group, $R^1$ represents n-propyl group, i.e., those having the formula

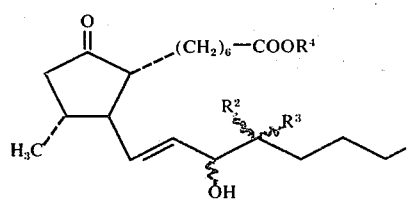

(I-a)

wherein $R^2$, $R^3$ and $R^4$ are the same as above and the pharmaceutically acceptable salt thereof. A most preferable group of the prostaglandin derivatives provided by the invention is those of the formula (I) wherein A represents hexamethylene group, $R^1$ represents n-propyl group and $R^2$ and $R^3$ each represent the alkyl group, i.e., those having the formula

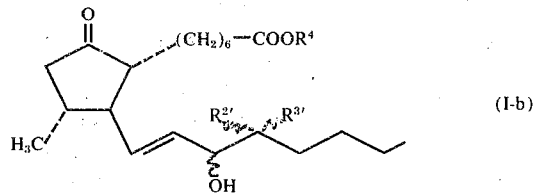

(I-b)

wherein $R^4$ is the same as above and $R^{2'}$ and $R^{3'}$ may be the same or different and each represents an alkyl group having 1–4 carbon atoms and the pharmaceutically acceptable salts thereof.

In formulae (I), (I-a) and (I-b), and elsewhere in this specification, a bond attached to the cyclopentane nucleus which is in the α-configuration, i.e., extends below the plane of the cyclopentane ring, is represented by a dotted line, and a bond which is in the β-configuration, i.e., extends above the plane of the cyclopentane ring, is represented by a solid line. The wavy line indicates that either steric configuration is possible.

The pharmaceutically acceptable salts of the acids of formulae (I), (I-a) and (I-b) in which $R^4$ is hydrogen atom include alkali and alkaline earth metal salts, e.g., the sodium, potassium, magnesium and calcium salts, quaternary ammonium salts, e.g., the ammonium, tetramethylammonium, tetraethylammonium, benzyltrimethylammonium and phenyltriethylammonium salts, aliphatic, alicyclic or aromatic amine salts, e.g., the methylamine, ethylamine, dimethylamine, diethylamine, trimethylamine, triethylamine, N-methylhexylamine, cyclopentylamine, dicyclohexylamine, benzylamine, dibenzylamine, α-phenylethylamine and ethylenediamine salts, heterocyclic amine salts, e.g., the piperidine, morpholine, pyrrolidine, piperazine, pyridine, 1-methylpiperazine and 4-ethylmorpholine salts, salts of amines which are water-soluble or contain a hydrophilic group, e.g., the monoethanolamine, ethyldiethanolamine and 2-amino-1-butanol salts. Such salts may be prepared from the acids of formulae (I), (I-a) (I-b) in which $R^4$ is hydrogen atom by the conventional techniques. Heretofore anti-ulcerogenic effects of prostaglandins $E_1$ and $E_2$ have been reported by Ruth Partridge et al., in U.S. Pat. No. 3,781,429 and by A. Robert in Prostaglandins, June 25, 1974, vol. 6, No. 6, pages 523 – 532. However, they exhibit simultaneously potent hypotensive and intestinal tube-contracting activities which are troublesome to anti-ulcerogenic agents. It has been also reported by Abraham Nedumparambil Abraham et al. in German Patent Offenlegungsschrift 2,313,868 that 9-oxo-11β-methyl-15α(or β)-hydroxyprost-13(trans)-enoic acid inhibit gastric secretion. However, anti-ulcerogenic activity of the compound is extremely lower than that of prostaglandins $E_1$ and $E_2$.

As a result of our research, we have found that the present prostaglandin derivatives inhibit, by oral administration, the ulcerogenic effect induced by anti-inflammatory agents such as indomethacin, phenylbutazone and aspirin or induced by stress. On the other hand, they exhibit no or little hypotensive and intestinal tube-contracting activity.

The anti-ulcerogenic activity of the present prostaglandin derivatives will be evident from the following pharmacological comparative test data.

1. Inhibition of indomethacin-induced gastric ulceration by prostaglandins

METHOD

The method employed for the production and evaluation of indomethacin-induced ulcers was essentially same as described by Lee, Mollison and Cheng in Archives Internationales de Pharmacodynamie et de Therapie, vol. 191, page 370 – 377 and by Lippmann in Prostaglandins, vol. 7, page 1 – 10. Sprague-Dawley strain male rats weighing 200 – 220 g were fasted 20 hours with free access to water until the start of experiment. Indomethacin was suspended in 0.4% Tween 80 (surface active agent, product of Atlas Powder Co. U.S.A.) solution and given intraperitoneally into the rats at a dose of 30 mg/kg body weight. The test drugs were dissolved in physiological saline with aid of an ultrasonicator and administered perorally immediately after the administration of indomethacin. The animals were killed 5 hours later and the ulcer formation in the glandular portion of the stomach was determined.

RESULT

The tested prostaglandins inhibited the indomethacin-induced gastric ulceration in rats. Table 1 shows the results.

TABLE 1

Inhibitory effects of prostaglandins on the indomethacin-induced gastric ulceration in rats.

| Drug | Dose (mg/kg p.o.) | No. of animals | Inhibitory ratio (%) | $ED_{50}$(mg/kg) (50% inhibition of the ulcer formation) |
|---|---|---|---|---|
| Compound A | 0.25 | 10 | 63 | 0.16 |
|  | 0.50 | 16 | 71 |  |
| Compound B | 0.25 | 20 | 49 | 0.26 |
|  | 0.50 | 18 | 67 |  |
| Compound C | 1.25 | 5 | 52 | 1.18 |
|  | 2.5 | 13 | 68 |  |
| Compound D | 1.25 | 5 | 43 | 1.64 |
|  | 2.5 | 5 | 61 |  |
| $PGE_2$ | 0.05 | 10 | 57 | 0.03 |
|  | 0.25 | 9 | 79 |  |

Compound A:
9-Oxo-11α,16,16-trimethyl-15α-hydroxyprost-13(trans)-enoic acid.
Compound B:
Methyl 9-oxo-11α,16,16-trimethyl-15α-hydroxyprost-13(trans)-enoate.
Compound C:
9-Oxo-11α-methyl-15α-hydroxyprost-13(trans)-enoic acid
Compound D:
9-Oxo-11β-methyl-15α-hydroxyprost-13(trans)-enoic acid (known compound)

$PGE_2$ was approximately 5 times more potent than the compound A in inhibition of the indomethacin-induced ulcer formation. However $PGE_2$ exhibits various side effects including diarrhea and vasode-pressor activity. The prostaglandin derivatives of this invention show very low diarrheal activity (1% of $PGE_2$), no vasode-press or activity and no inhibition of platelet aggregation. Therefore, it can be said that the prostaglandin derivatives of this invention exhibit more selectively anti-ulcer effects.

2. Inhibition of the stress-induced ulceration by prostaglandins

METHOD

The method employed for the production and evaluation of stress ulcer was essentially same as described by Takagi and Okabe in Journal of Pharmacology vol. 18, pages 9–18 (Japan). Donryu strain male rats, 200 – 230 g in weight, were used. Animals were placed in the stress cage and immersed in a water bath kept at 23° C for 8 hr to the height of the xiphoid of the animal. At the end of the stress, the animals were killed by a blow, and stomach was removed, inflated with 10 ml of 1% formalin solution and placed into 1% formalin solution. Thereafter the stomach was cut along the greater curvature and examined for lesions macroscopically. The ulcer index was calculated as the sum of the length of each lesion in the stomach. Inhibitory ratio of ulceration was calculated for each dose. The test drugs were dissolved into 0.4% Tween 80 solution with aid of an ultrasonicator and administered orally (0.2 ml/100 g) immediately before the stress.

RESULT

The tested prostaglandins inhibited the stress-induced ulceration in rats. Table 2 shows the results. Compound A and B exhibited anti-stress ulcer activity equally potent as or slightly more potent than that of $PGE_2$ and significantly more potent than that of $PGE_1$. Compound A and B were more than 10 times potent as Compound C.

| Drug | Dose (mg/kg p.o.) | No. of animals | Inhibitory ratio (%) |
|---|---|---|---|
| Compound A | 0.3 | 10 | 12 |
|  | 1.0 | 10 | 73 |
| Compound B | 0.3 | 10 | 11 |
|  | 1.0 | 5 | 92 |
| Compound C | 5.0 | 5 | 9 |
|  | 10 | 10 | 40 |
| $PGE_1$ | 1.0 | 15 | 0 |
|  | 3.0 | 5 | 98 |
| $PGE_2$ | 0.3 | 25 | 17 |
|  | 1.0 | 10 | 60 |

It is evident from the data given above that the prostaglandin derivatives of this invention are useful as anti-ulcer agents. The compounds of this invention are administered orally or parenterally, preferably orally, in accordance with conventional procedures, for example, in the form of tablets, capsules, injectable liquids and suspensions. The dosage may be varied depending upon ages, condition and weight of a patient. The compounds of this invention are usually administered in an amount of from about 0.5 mg to about 100 mg per day for adult in divided dosage, e.g., three or four times a day.

According to the present invention, the compounds having the formula (I) may be prepared by reducing a compound having the formula

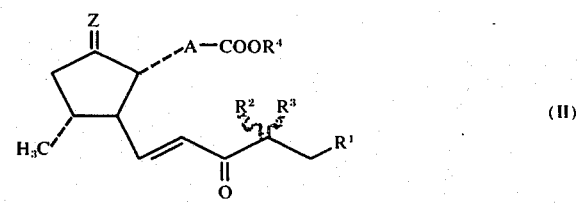

(II)

wherein A, $R^1$, $R^2$, $R^3$ and $R^4$ are the same as above and Z represents a carbonyl-protecting group to give a compound having the formula

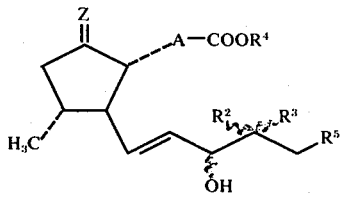

(III)

wherein A, $R^1$, $R^2$, $R^3$, $R^4$ and Z are the same as above and removing the carbonyl-protecting group of the latter compound.

Preferable examples of the carbonyl-protecting group include an oxime group; a dialkoxy group having 1 – 5 carbon atoms in each alkyl moiety, e.g., dimethoxy and diethoxy; an alkylenedioxy group having 1 – 5 carbon atoms, e.g., methylenedioxy and ethylenedioxy; and an alkylenedithio group having 1 – 5 carbon atoms, e.g., ethylenedithio and trimethylenedithio.

The reduction may be preferably carried out by contacting the compound (II) with a metal hydride complex in the presence of an inert organic solvent. Preferable examples of the metal hydride complex include alkali metal boron hydrides, e.g., sodium boron hydride, potassium boron hydride, lithium boron hydride, sodium cyano boron hydride, lithium $9b$-boroperhydrophenalene hydride; alkali metal aluminum hydrides, e.g., aluminum tri-tert-butoxylithium hydride, aluminum trimethoxylithium hydride; and zinc boron hydride. Preferable examples of the inert organic solvent include alcohols, e.g., methanol and ethanol; ethers, e.g., diethyl ether, tetrahydrofuran, dioxane, diglyme; and dialkylformamides, e.g., dimethylformamide. The reduction is preferably carried out at relatively low temperatures, usually at a temperature from −10° C to room temperature. The reaction period will depend mainly upon the reaction temperature and kind of the reducing agent. It is usually from about 30 minutes to 5 hours. The reduction may be also carried out by Meerwein-Pondarf-Verley Reduction using aluminum isopropoxide and isopropanol.

After completion of the reaction, the desired product may be recovered from the reaction mixture by conventional means. For instance, organic acids, e.g., formic acid and acetic acid, are added to the reaction mixture in order to decompose the excess reducing agent and the mixture is extracted with an organic solvent. The extract is washed with water and dried and the solvent is distilled off to give the desired product. The product thus obtained may be further purified, if necessary, by conventional means, for example, column chromatography or thin-layer chromatography. The reaction for eliminating the carbonyl-protecting group may vary depending on the kind of the protecting group used. In cases where the protecting group is, for example, oxime, it may be removed by being contacted with an acid. The acid used is preferably a mineral acid, such as, for example, hydrochloric acid, sulfuric acid and nitrous acid and an organic acid, such as, for example, pyruvic acid. In cases where the protecting group is, for example, dialkoxy group, such as, for example, dimethoxy and diethoxy, alkylenedioxy group, such as, for example, methylenedioxy and ethylenedioxy, it may be removed by being contacted with an acid. The acid used is preferably an organic acid, such as, for example, formic acid, acetic acid, propionic acid, butyric acid, oxalic acid, malonic acid, p-toluenesulfonic acid and picric acid, and a mineral acids, such as, for example, hydrochloric acid, hydrobromic acid and sulfuric acid. In cases where the protecting group is, for example, alkylenedithio group, such as ethylenedithio and trimethylenedithio, it may be removed by being contacted with mercuric chloride. The reaction may be preferably carried out in the presence of solvent. The solvent used is not limited so far as the solvent is inert to the present reaction, and is preferably water; alcohols, such as methanol and ethanol; ethers, such as tetrahydrofuran and dioxane; ketone, such as acetone; or mixed solvents of the said organic solvent with water. The reaction temperature is not limited, but is preferably at temperatures from room temperature to about 60° C. The reaction time may vary mainly depending on the kind of a protecting group to be removed and the conditions of removing reaction employed.

After completion of the reaction, the object compound (II) may be recovered from the reaction mixture by means of a common method. For example, it is obtained by, after the reaction, neutralizing the reaction mixture by adding a base such as sodium acetate thereto, evaporating the solvent from the reaction mixture, extracting the resulting residue by adding an organic solvent thereto, washing the extract with water followed by drying, and evaporating the solvent from the extract. The object compound thus obtained may be further purified, if necessary, by means of a usual method, such as, for example, column chromatography and thin-layer chromatography.

The compounds of the formula (I) and their salts can exist as four different optical isomers, depending upon the configuration of the hydroxyl groups attached to the cyclopentane nucleus and the side-chain. The racemic mixtures of these isomers can be resolved by the conventional techniques, so as to obtain the desired products in the form of optically pure diastereoisomers. The formulae (I), (I-a) and (I-b) are used to represent both diastereoisomeric forms, as well as the racemic mixtures, but the pure isomers are included within the scope of the invention, as well as their mixtures. The group $R^4$ may be removed by conventional means, for example, by treating with an acid, e.g., acetic acid, hydrochloric acid or with a base, e.g., sodium hydroxide, sodium carbonate.

The compounds of a formula (II), employed as a starting materials in the preparation of the compounds of the invention, are also novel and can be prepared by the process shown in the following reaction schemes.

Preparation of the starting compound (II)

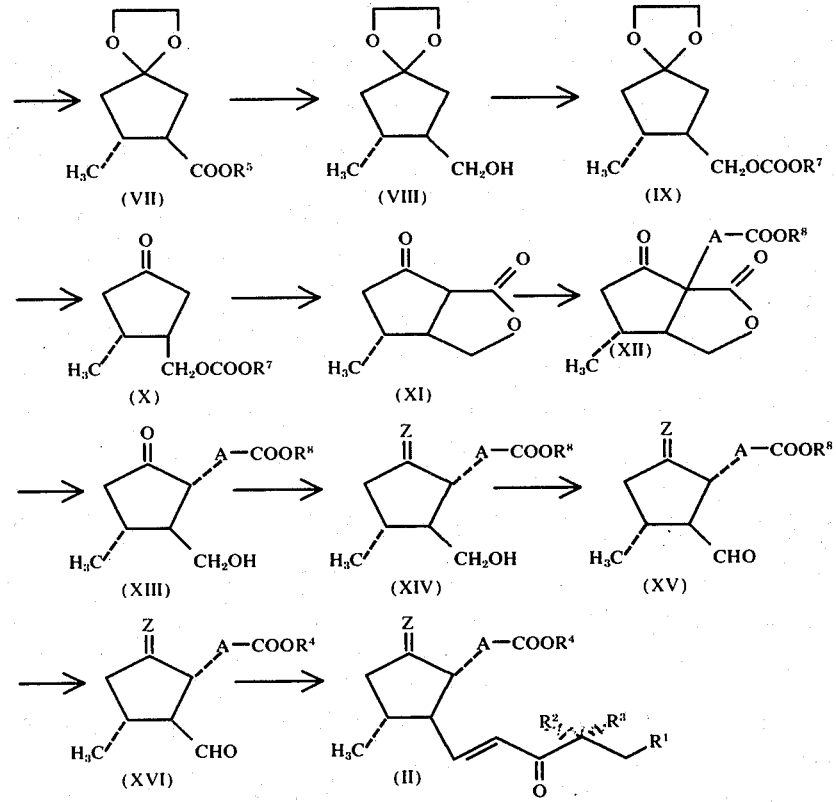

J.Org.Chem.33,4508(1968)

In the above scheme, A, $R^1$, $R^2$, $R^3$, $R^4$ and Z are the same as above and $R^5$, $R^6$, $R^7$ and $R^8$ may be the same or different and each represents an alkyl group having 1 – 6 carbon atoms.

Each of the above steps may be illustrated as follows: The compound (V) may be prepared by reacting the compound (IV) with an alkali metal halide and an organic acid. Examples of the alkali metal halide include sodium iodide, sodium bromide, potassium iodide and potassium bromide. Examples of the organic acid include acetic acid and propionic acid. The reaction is preferably carried out in an inert organic solvent such as benzene, methanol, ethanol, dioxane, ether or diethylene glycol dimethyl ether at temperatures from about 80° to about 150° C.

The compound (VI) may be prepared by reacting the compound (V) with ethylene glycol in the presence of a Lewis acid, e.g., boron trifluoride.

The reaction is preferably carried out in an inert organic solvent such as dichloromethane, chloroform or benzene at temperatures for 0° C to room temperature.

The compound (VII) may be prepared by reacting the compound (VI) with an alkali metal compound, e.g., sodium methoxide, potassium ethoxide, sodium hydroxide. The reaction is preferably carried out in an inert organic solvent such as tetrahydrofuran, dioxane or methanol at temperatures from 0° C to a reflux temperature of the reaction mixture.

The compound (VIII) may be prepared by reducing the compound (VII) with a metal hydride compound such as sodium boron hydride, potassium boron hydride, lithium boron hydride, trimethoxylithium aluminum hydride and aluminum lithium hydride. The reaction is preferably carried out in an inert organic solvent such as methanol, tetrahydrofuran or ether at temperatures from 0° C to a reflux temperature of the reaction mixture.

The compound (IX) may be prepared by reacting the compound (VIII) with a compound having the formula $$X^1—COOR^7$$

wherein $R^7$ is the same as above and $X^1$ represents a halogen atom, e.g., chlorine, bromine, iodine in the presence of a base such as sodium carbonate, sodium bicarbonate, triethylamine, pyridine or N-methylpiperizine. The reaction is preferably carried out below room temperature.

The compound (X) may be prepared by reacting the compound (IX) with an acid such as formic acid, acetic acid, hydrochloric acid, hydrobromic acid or sulfuric acid. The reaction is preferably carried out in a solvent such as water, methanol, ether or acetone at temperatures from 0° to 60° C.

The compound (XI) may be prepared by reacting the compound (X) with a base such as alkali metal alkoxides, e.g., sodium methoxide, potassium ethoxide, potassium tert-butoxide; alkali metal hydrides, e.g., sodium hydride, potassium hydride; or alkali metal hydroxides, e.g., sodium hydroxide, potassium hydroxide. The reaction is preferably carried out in an inert organic solvent such as tetrahydrofuran, ether and benzene at temperatures from −50° C to 80° C in an inert gas, e.g., argon, helium.

The compound (XII) may be prepared by reacting the compound (XI) with a compound having the formula $$X^2-A-COOR^8$$

wherein A and $R^8$ are the same as above and $X^2$ represents a halogen atom, e.g., iodine, bromine, chlorine, in the presence of a base such as alkali metals, e.g., metallic sodium, alkali metal hydroxides, e.g., sodium hydroxide, potassium hydroxide; or alkali metal alkoxides, e.g., sodium methoxide, potassium ethoxide. The reaction is preferably carried out in an inert organic solvent, e.g., benzene, ether, tetrahydrofuran, hexamethyl phosphoramide, dimethyl sulfoxide, below room temperature in an inert gas, e.g., argon, helium.

The compound (XIII) may be prepared by reacting the compound (XII) with a base such as sodium hydroxide, ammonium acetate, sodium phosphate-dibasic, potassium hydroxide, sodium carbonate or potassium carbonate. The reaction is preferably carried out in a solvent, e.g., water, methanol, ether, dioxane, a mixture of water and such an organic solvent, at temperatures from room temperature to reflux temperature of the reaction mixture in an inert gas, e.g., argon, helium.

The compound (XIV) may be prepared by contacting the compound (XIII) with a compound capable of forming a carbonyl-protecting group. Preferable examples of the compound which can form a carbonyl-protecting group include hydroxylamines such as hydroxylamine or methylhydroxylamine sodium hydroxylaminesulfonate which form an oxime group; orthoformic acid esters such as methyl orthoformate, ethyl orthoformate, which form a ketal group; alkylene glycols such as methylene glycol or ethylene glycol, which form a ring ketal group; and alkylene dithioglycol such as ethylene dithioglycol or trimethylene dithioglycol, which form a thioketal ring.

The reaction of the compound (XIII) with the hydroxylamines is carried out in the presence of a base, e.g., sodium hydroxide. The reaction of the compound (XIII) with orthoformic acid esters, alkylene glycols or alkylene dithioglycols is carried out in the presence of a small amount of acids, for example, mineral acids such as hydrochloric acid or sulfonic acid, organic acids such as benzenesulfonic acid, p-toluenesulfonic acid, picric acid or trifluoroacetic acid and Lewis acids such as boron trifluoride, aluminum chloride or zinc chloride. When orthoformic acid esters are used as a reagent, there may be preferably employed concentrated sulfonic acid or hydrogen chloride. When alkylene glycols are used as a reagent, there may be preferably employed p-toluenesulfonic acid. The reaction may be preferably carried out in the presence of a solvent such as benzene, toluene, dichloromethane or chloroform. The reaction is usually carried out at reaction temperatures from room temperature to a reflux temperature of the reaction mixture. When the mineral acids or Lewis acids are used, the reaction is preferably carried out at −20° C to room temperature. When organic acids are used, the reaction is preferably carried out at an approximate reflux temperature of the solvent used.

The compound (XV) may be prepared by contacting the compound (XIV) with an oxidizing agent such as chromic acid, chromic anhydride, chromic anhydride-pyridine complex, sodium bichromate, dimethyl sulfoxide-chlorine complex, methyl sulfide-N-chlorosuccinimide. The reaction is preferably carried out in a solvent such as acetic acid, dichloromethane, chloroform at temperatures from 0° C to room temperature.

In case where the compounds having the formula (XVI) in which $R^4$ is hydrogen atom are desired, the compound (XVI) may be prepared by contacting the compound (XV) with an acid such as formic acid, acetic acid, hydrochloric acid or sulfuric acid, or with a bases such as sodium hydroxide, potassium hydroxide or sodium carbonate. The reaction is preferably carried out in a solvent, e.g., water, methanol, ether, at temperatures from room temperature to reflux temperature of the reaction mixture.

The compound (II) may be prepared by reacting the compound (XVI) with a Wittig reagent having the formula

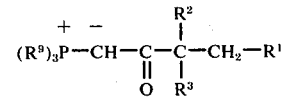

wherein $R^1$ is the same as above and $R^9$ represents an alkyl group having 2 – 5 carbon atoms or a phenyl group. At least one mole of the Wittig reagent is used per mole of the compound (XVI) and preferably from 2 to 10 moles of the Wittig agent is used.

The reaction is generally carried out in an inert organic solvent such as ether, benzene, toluene, hexane, dimethyl sulfoxide, tetrahydrofuran, methylene chloride or chloroform, at temperatures of from 0° C to a reflux temperature of the reaction mixture, preferably at room temperature or below and in an inert gas, e.g., argon, helium. The reaction is carried out for a period of 5 hours to 30 hours depending on the temperature and concetration of the reaction mixture and the specific Wittig reagent used.

The product obtained in each step of the above process may be recovered from the reaction mixture in a conventional manner, for example, by evaporating the solvent from the reaction mixture or by adding water and extracting with a water-immiscible solvent. The crude product can be purified by conventional means such as recrystallization or chromatography.

The following preparations and examples are given for the purpose of illustration of the present invention.

PREPARATION 1

Preparation of methyl 9-ethylenedioxy-11α,16,16-trimethyl-15-oxoprost-13(trans)-enoate (II)

1. 3α-Methyl-4α-ethoxycarbonylcyclopentanone (V)

In 250 ml of diethylene glycol dimethyl ether was dissolved 70 g of 260-methoxycarbonyl-3α-methyl-4α-ethoxycarbonylcyclopentanone and to the solution were added 25 ml of glacial acetic acid and 165 g. of sodium iodide. The mixture was refluxed for one hour. After completion of the reaction, the reaction mixture was cooled, diluted with 1.5 l of water and saturated with sodium chloride. The mixture was extracted with ether. The extract was washed with water, dried over anhydrous sodium sulfate and evaporated to dryness under reduced pressure. The oily residue was distilled in a high vacuum and passed over at 74° – 77° C under 0.9 mm pressure of mercury to give 39.8 g of the desired product.

I.R.(liquid film) $\nu_{max}^{cm^{-1}}$ :
1745, 1730, 1200

N.M.R. (CDCl$_3$) δ : ppm 1.10 (3H, doublet, —CH$_3$)

1.30 (3H, triplet, —CH$_2$CH$_3$)

4.25 (2H, quartet, —CH$_2$CH$_3$)

2. 1-Ethylenedioxy-3α-methyl-4α-ethoxycarbonylcyclopentane (VI)

In 700 ml of benzene was dissolved 39.8 g of 3α-methyl-4α-ethoxycarbonylcyclopentanone and to the solution were added 45 ml of ethylene glycol and 0.5 g of p-toluenesulfonic acid. The mixture was refluxed for 6 hours under removing the produced water by azeotropic distillation. The lost benzene was supplemented with an equivalent amount of benzene at an interval of one hour. After completion of the reaction, the reaction mixture was cooled, washed with a saturated aqueous sodium hydrogencarbonate and water and dried over anhydrous sodium sulfate. The solvent was distilled off under reduced pressure to give 50.2 g of the desired product as oil.

I.R. (liquid film) $\nu_{max}^{cm^{-1}}$ :
1735, 1730, 1330, 1180, 1040

N.M.R. (CDCl$_3$) δ : ppm 1.05 (3H, doublet, —CH$_3$)

1.28 (3H, triplet, —CH$_2$CH$_3$)

3.88 (4H, singlet, CH$_2$—CH$_2$)

4.13 (2H, quartet, —CH$_2$CH$_3$)

Mass spectrum M$^+$ : 214 (C$_{11}$H$_{18}$O$_4$)

3. 1-Ethylenedioxy-3α-methyl-4β-ethoxycarbonylcyclopentane (VII)

0.6 g of metallic sodium was dissolved in 50 ml of ethanol to which was added 50 ml of benzene. To the mixture was added 5.0 g of 1-ethylenedioxy-3α-methyl-4α-ethoxycarbonylcyclopentane, followed by stirring for 3 hours at 60° C. The reaction mixture was cooled, diluted with 150 ml of ice water and saturated with sodium chloride. The mixture was extracted twice with 250 ml of ether. The extract was washed with water, dried over anhydrous sodium sulfate and evaporated to dryness to afford 2.2 g of the desired product as oil.

I.R. (liquid film) $\nu_{max}^{cm^{-1}}$ :
1730, 1330, 1160, 1040

N.M.R. (CDCl$_3$) δ : ppm 1.10 (3H, doublet, —CH$_3$)

1.25 (3H, triplet, —CH$_2$CH$_3$)

3.90 (4H, singlet, CH$_2$—CH$_2$)

4.16 (2H, quartet, —CH$_2$CH$_3$)

Mass spectrum M$^+$: 214 (C$_{11}$H$_{18}$O$_4$)

4. 1-Ethylenedioxy-3α-methyl-4β-hydroxymethylcyclopentane (VIII)

11.0 g of lithium aluminum hydride was dissolved in 900 ml of anhydrous ether. The solution was stirred in argon atmosphere maintaining the inner temperature at 5° C. To the solution was added dropwise a solution of 61.4 g of 1-ethylenedioxy-3α-methyl-4β-ethoxycarbonylcyclopentane in 150 ml of anhydrous ether. After completion of the addition, the mixture was stirred at room temperature for 30 minutes and cooled. 62 ml of ethyl acetate was added to the mixture and stirred for 20 minutes. 48 ml. of 5% aqueous sodium hydroxide was added to the mixture and stirred for 1.5 hours. After completion of the reaction, the insolubles were filtered off and washed with chloroform. The solvent was distilled off from the filtrate and the washings under reduced pressure to give 48.0 g of the desired product as oil.

I.R. (liquid film) $\nu_{max}^{cm^{-1}}$ :
3450, 1320, 1040, 1015

N.M.R. (CDCl$_3$) δ : ppm 1.08 (3H, doublet, —CH$_3$)

2.48 (1H, singlet, —OH)

3.62 (2H, multiplet, —CH$_2$OH)

3.87 (4H, singlet, CH$_2$—CH$_2$)

5. 1-Ethylenedioxy-3α-methyl-4β-ethoxycarbonyloxymethylcyclopentane (IX)

49.0 g of 1-ethylenedioxy-3α-methyl-4β-hydroxymethylcyclopentane was dissolved in a mixture of 300 ml of pyridine and 200 ml of anhydrous benzene and to the solution was added dropwise 60.5 g of ethyl chloroformate under ice-cooling, followed by stirring at room temperature for 20 minutes. After completion of the reaction, the mixture was diluted with 500 ml of ice water and extracted twice with 200 ml of ethyl acetate. The extracts were washed with water, dried over anhydrous sodium sulfate and evaporated to dryness to give 68.0 g of the desired product as oil.

I.R. (liquid film) $\nu_{max}^{cm^{-1}}$:
1745, 1260, 1010
N.M.R. (CDCl₃) δ : ppm
1.05 (3H, doublet, —CH₃)

3.88 (4H, singlet, CH₂—CH₂) 
           |    |
           O    O 4.10 (2H, multiplet, —CH₂OCOO—)

4.17 (2H, quartet, —OCH₂CH₃)

6. 3α-methyl-4β-ethoxycarbonyloxymethylcyclopentanone (X)

68.0 g of 1-ethylenedioxy-3α-methyl-4β-ethoxycarbonyloxymethylcyclopentane was dissolved in 600 ml of acetone. To the mixture was added 80 ml of 7% aqueous hydrochloric acid under ice-cooling, followed by stirring at room temperature for 2 hours. After completion of the reaction, the mixture was diluted with 1.3 l of water and saturated with sodium chloride. The mixture was extracted with 500 ml of benzene and then re-extracted with 500 ml of ethyl acetate. The extract was washed with a saturated aqueous sodium chloride, dried over anhydrous sodium sulfate and evaporated to dryness under reduced pressure to give 55.0 g of the desired product as oil.

I.R. (liquid film) $\nu_{max}^{cm^{-1}}$:
1740, 1260, 1010, 795

N.M.R. (CDCl₃) δ : ppm
1.12 (3H, doublet, —CH₃)

1.30 (3H, triplet, —CH₂CH₃)

4.18 (2H, quartette, —CH₂CH₃)

4.20 (2H, multiplet, —CH₂OCOO—)

Mass spectrum M⁺ : 200.2 (C₁₀H₁₆O₄)

7. 2β-Carboxy-3β-hydroxymethyl-4α-methylcyclopentanone-2,3(γ)-lactone (XI)

48.0 g of 3α-methyl-4β-ethoxycarbonyloxymethylcyclopentanone was dissolved in 300 ml of anhydrous tetrahydrofuran. To the solution was added a suspension of 50.0 g of potassium tert-butoxide (crystals containing one molecule of tert-buthanol) in 1 l of anhydrous tetrahydrofuran in argon atmosphere at temperatures ranging from −40° C to −30° C for one hour. After completion of the reaction, 30 ml of glacial acetic acid was added to the reaction mixture and the solvent was distilled off under reduced pressure. To the residue were added 1 l of ether and 1 l of benzene and the crystals produced were filtered off. The solvent was distilled off from the filtrate under reduced pressure to give 40 g of an oily residue which was recrystallized from a mixture of ethyl acetate and n-hexane to give 23.8 g of the desired product as crystal melting at 81° – 83° C.

I.R. (Nujol) $\nu_{max}^{cm^{-1}}$:
1770, 1725, 1180, 1150, 1040
N.M.R. (CDCl₃) δ : ppm
1.27 (3H, doublet, —CH₃)

3.48 (1H, doublet, 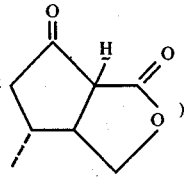 )

4.1 – 4.7 (2H, multiplet, 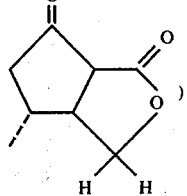 )

8. 2β-Carboxy-3β-hydroxymethyl-2α-(6-methoxycarbonylhexyl)-4α-methylcyclopentanone-2,3(γ)-lactone (XII)

23.5 g of 2β-carboxy-3β-hydroxymethyl-4α-methylcyclopentanone-2,3(γ)-lactone was dissolved in 400 ml of hexamethylphosphoroamide. To the solution was added a solution of 31.2 g of potassium tert-butoxide (crystal containing one molecule of tert-butanol) in 95 ml of hexamethylphosphoroamide in argon atmosphere at temperatures ranging 10° C to 15° C for 20 minutes. To the mixture was added 47.4 g of methyl 7-iodoenanthoate at temperatures ranging from 8° to 15° C for 30 minutes, followed by stirring for 1 hour. After completion of the reaction, the mixture was diluted with 2 l of ice water containing 20 ml of acetic acid and saturated with sodium chloride. The mixture was extracted three times with 700 ml of benzene. The extracts were washed with water, dried over anhydrous sodium sulfate and evaporated to dryness to give an oily residue which was recrystallized from a mixture of ethyl acetate and n-hexane to give 34.9 g of the desired product as crystal melting at 62.5° – 64.5° C.

I.R. (Nujol) $\nu_{max}^{cm^{-1}}$:
1780, 1740, 1190, 1170
N.M.R. (CDCl₃) δ : ppm
1.25 (3H, doublet, —CH₃)

3.70 (3H, singlet, —COOCH₃)

4.34 (2H, multiplet, 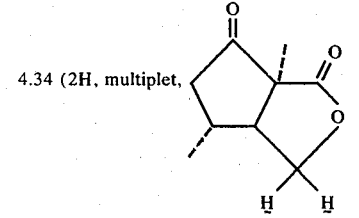 )

9. 2α-(6-Methoxycarbonylhexyl)-3β-hydroxymethyl-4α-methylcyclopentanone (XIII)

10.5 of 2β-carboxy-3β-hydroxymethyl-2α-(6-methoxycarbonylhexyl)-4α-methylcyclopentanone-2,3(γ)-lactone was dissolved in a mixture of 500 ml of methanol and 1000 ml of 10% aqueous sodium acetate, followed by heating under reflux for 4 hours. The reaction mixture was cooled, diluted with 1 l of water and saturated with sodium chloride. The mixture was extracted with 500 ml of benzene and re-extracted with 200 ml of ether. The extract was washed successively with 5% aqueous potassium carbonate and water, dried over anhydrous sodium sulfate and evaporated to dryness under reduced pressure to give 8.4 g of an oily residue which was recrystallized from a mixture of ether and n-hexane to afford 2.7 g of the unreacted starting material. The mother liquor was subjected to column chromatography using 60 g of silica gel to give 3.75 g of the desired product as oil.

I.R. (liquid film) $\nu_{max}^{cm-1}$ :
  3450, 1740, 1170, 1065

N.M.R. (CDCl$_3$) δ : ppm
  1.16 (3H, doublet, —C$\underline{H}_3$)
  3.68 (3H, singlet, —COOC$\underline{H}_3$)
  3.87 (2H, doublet, —C$\underline{H}_2$OH)

10. 1-Ethylenedioxy-2α-(6-methoxycarbonylhexyl)-3β-hydroxymethyl-4α-methylcyclopentane (XIV)

3.6 g. of 2α-(6-methoxycarbonylhexyl)-3β-hydroxymethyl-4α-methylcyclopentanone was dissolved in 300 ml of benzene and to the solution were added 6 ml of ethylene glycol and 150 mg of p-toluenesulfonic acid. The mixture was refluxed for 3 hours under removing the produced water by azeotropic distillation. The lost benzene was supplemented with an equivalent amount of benzene at regular intervals. After completion of the reaction, the mixture was cooled, washed successively with 5% aqueous sodium hydrogencarbonate and water, dried over anhydrous sodium sulfate and evaporated to dryness under reduced pressure to give 4.1 g of the desired product as oil.

I.R. (liquid film) $\nu_{max}^{cm-1}$ :
  3500, 1740, 1200, 1175, 1025, 955
N.M.R. (CDCl$_3$) δ : ppm
  1.08 (3H, doublet, —C$\underline{H}_3$)
  3.65 (5H, singlet, —COOC$\underline{H}_3$ and —C$\underline{H}_2$OH)
  3.90 (4H, singlet, C$\underline{H}_2$—C$\underline{H}_2$ )
    |  |
    O  O
     \/
     /\

11. 1-Ethylenedioxy-2α-(6-methoxycarbonylhexyl)-3β-formyl-4α-methylcyclopentane (XV)

To a mixture of 250 ml of anhydrous dichloromethane and 15 ml of pyridine was added little by little 9.14 g of chromic anhydride at 15° C in argon atmosphere, followed by stirring at room temperature for 15 minutes. To the solution was added a solution of 4.1 g of 1-ethylenedioxy-2α-(6-methoxycarbonylhexyl)-3β-hydroxymethyl-4α-methylcyclopentane in 20 ml of anhydrous dichloromethane and stirred for 20 minutes. After completion of the reaction, the mixture was diluted with 1 l of ether and the insolubles were filtered off. The filtrate was washed successively with 3% aqueous sodium hydroxide, 3% aqueous hydrochloric acid, 5% aqueous sodium hydrogencarbonate and water, dried over anhydrous sodium sulfate and evaporated to dryness under reduced pressure to afford 3.8 g of the desired product as oil.

I.R. (liquid film) $\nu_{max}^{cm-1}$ :
  2720, 1740, 1720, 1200, 1170, 1025
N.M.R. (CDCl$_3$) δ : ppm
  1.05 (3H, doublet, —C$\underline{H}_3$)
  3.67 (3H, singlet, —COOC$\underline{H}_3$)
  3.90 (4H, broad singlet, C$\underline{H}_2$—C$\underline{H}_2$)
    |  |
    O  O
     \/
     /\
  9.47 (1H, doublet, —C$\underline{H}$O)

12. Methyl 9-ethylenedioxy-11α,16,16-trimethyl-15-oxoprost-13(trans)-enoate (II)

2.53 g of 1-ethylenedioxy-2α-(6-methoxycarbonylhexyl)-3β-formyl-4α-methylcyclopentane was dissolved in 60 ml of dioxane and to the solution was added 5.6 g of 2-oxo-3,3-dimethylheptylidenetri-n-butylphosphoran. The mixture was heated under reflux for 2 days. After completion of the reaction, the solvent was distilled off under reduced pressure from the reaction mixture and the residue was subjected to column chromatography using 250 g of alumina (product of Woelm Company, neutral, Grade III) to give 2.03 g of the desired product as oil.

I.R. (liquid film) $\nu_{max}^{cm-1}$ :
  1740, 1690, 1620, 1170, 1040
N.M.R. (CDCl$_3$) δ : ppm
  3.66 (3H, singlet, —COOC$\underline{H}_3$)
  3.90 (4H, singlet, C$\underline{H}_2$—C$\underline{H}_2$)
    |  |
    O  O
     \/
     /\

6.30 – 7.00 (2H, multiplet,  )

PREPARATION 2

Methy 9-ethylenedioxy-11α-methyl-15oxoprost-13(trans)-enoate (II)

3.85 g of 1-ethylenedioxy-2α-(6-methoxycarbonylhexyl)-3β-formyl-4α-methylcyclopentane was dissolved in 50 ml of ether and to the solution was added 5.0 g of 2-oxo-heptylidenetri-n-butylphosphoran. The mixture was stirred at room temperature overnight in argon atmosphere. The solvent was distilled off from the reaction mixture and the residue was subjected to column chromatography using 300 g of alumina (product of Woelm Company, neutral, Grade III) to give 3.7 g of the desired product as oil.

I.R. (liquid film) $\nu_{max}^{cm-1}$ :
  1740, 1690, 1670, 1625, 1195, 1170, 1030
N.M.R. (CDCl$_3$) δ : ppm
  0.94 (3H, doublet, —C$\underline{H}_3$)
  3.65 (3H, singlet, —COOC$\underline{H}_3$)

3.90 (4H, broad, C$\underline{H}_2$—C$\underline{H}_2$) 

6.10 (1H, doublet, 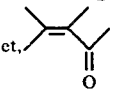)

6.45 – 6.88 (1H, multiplet, )

Mass spectrum M$^+$ : 408 (C$_{24}$H$_{40}$O$_5$)

U.V. λ$_{max}^{Ethanol}$ : 230.6 nm (ε = 13900)

PREPARATION 3

Methyl 9-ethylenedioxy-11α-methyl-15-oxo-20-ethylprost-13(trans)-enoate (II)

2.54 g of 1-ethylenedioxy-2α(6-methoxycarbonylhexyl)-3β-formyl-4α-methylcyclopentane was dissolved in 50 ml of ether and to the solution was added 3.0 g of 2-oxononylidenetri-n-butylphosphoran. The mixture was stirred at room temperature for 16 hours. The solvent was distilled off under reduced pressure from the reaction mixture and the residue was subjected to column chromatography using 210 g of alumina (product of Woelm Company, neutral, Grade III) to give 2.84 g of the desired product as oil.

I.R. (liquid film) ν$_{max}^{cm^{-1}}$:
1740, 1690, 1670, 1630, 1200, 1170, 1030
N.M.R. (CDCl$_3$) δ : ppm
3.67 (3H, singlet, —COOC$\underline{H}_3$
3.90 (4H, singlet, C$\underline{H}_2$—C$\underline{H}_2$) 

6.08 (1H, doublet, 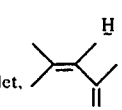)

6.46 – 6.90 (1H, multiplet, 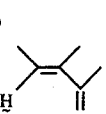)

PREPARATION 4

Methyl 9-ethylenedioxy-11α,20-dimethyl-15-oxo-prost-13(trans)-enoate (II)

2.14 g of 1-ethylenedioxy-2α-(6-methoxycarbonylhexyl)-3β-formyl-4α-methylcyclopentane was dissolved in 50 ml of ether and to the solution was added 2.8 g of 2-oxooctylidenetri-n-butylphosphoran. The mixture was stirred at room temperature for 16 hours. The solvent was distilled off under reduced pressure from the reaction mixture and the residue was subjected to column chromatography using 150 g of alumina (product of Woelm Company, neutral, Grade III) to give 2.04 g of the desired product as oil.

I.R. (liquid film) ν$_{max}^{cm^{-1}}$ :
1740, 1690, 1670, 1630, 1195, 1170, 1035, 985
N.M.R. (CDCl$_3$) δ : ppm
3.68 (3H, singlet,—COOC$\underline{H}_3$)
3.92 (4H, singlet, C$\underline{H}_2$—C$\underline{H}_2$) 

6.08 (1H, doublet, )

6.68 (1H, multiplet, 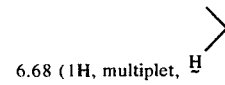)

PREPARATION 5

Methyl 9-ethylenedioxy-11α-methyl-15-oxo-20-n-propylprost-13(trans)-enoate (II)

2.22 g of 1-ethylenedioxy-2α-(6-methoxycarbonylhexyl)-3β-formyl-4α-methylcyclopentane was dissolved in 50 ml of ether and to the solution was added 3.04 g of 2-oxodecylidenetri-n-butylphosphoran. The mixture was stirred at room temperature for 16 hours. The solvent was distilled off under reduced pressure from the reaction mixture and the residue was subjected to column chromatography using 190 g of alumina (product of Woelm Company, neutral, Grade III) to give 2.58 g of the desired product as oil.

I.R. (liquid film) ν$_{max}^{cm^{-1}}$ :
1740, 1695, 1670, 1628, 1195, 1170
N.M.R. (CDCl$_3$) δ : ppm
3.68 (3H, singlet, —COOC$\underline{H}_3$)

3.90 (4H, singlet, C$\underline{H}_2$—C$\underline{H}_2$ ) 

6.08 (1H, doublet )

6.70 (1H, multiplet, )

EXAMPLE 1

Methyl 9-oxo-11α,16,16-trimethyl-15α(or β)-hydroxyprost-13(trans)-enoate (I)

1. Methyl 9-ethylenedioxy-11α,16,16-trimethyl-15-hydroxyprost-13(trans)-enoate (III)

1.95 g of methyl 9-ethylenedioxy-11α,16,16-trimethyl-15-oxoprost-13(trans)-enoate was dissolved in 60 ml of absolute methanol. To the solution was added 0.17 g of sodium boron hydride in argon atmosphere at temperatures ranging from 3° to 5° C, followed by stirring for one hour. The reaction mixture was diluted with 150 ml of ice water containing 1 ml of glacial acetic acid and saturated with sodium chloride. The mixture was extracted three times with 100 ml of ethyl acetate each time. The extracts were washed with water, dried over anhydrous sodium sulfate and evaporated to dryness to afford 1.96 g of oil which was purified by column chromatography using 50 g of silica gel to give 1.58 g of methyl 9-ethylenedioxy-11α,16,16-trimethyl-15-hydroxyprost-13(trans)-enoate as oil.

I.R. (liquid film) $\nu_{max}^{cm^{-1}}$:
  3500, 1740, 1200, 1170, 1030, 975
N.M.R. (CDCl$_3$) δ : ppm
  3.66 (3H, singlet, —COOC$\underline{H}_3$)
  3.87 (4H, singlet, C$\underline{H}_2$—C$\underline{H}_2$)
                    |      |
                    O      O
                     \    /
                      \  /
                       X

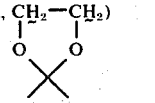
5.50 (2H, multiplet, $\underline{H}$

2. Methyl 9-oxo-11α,16,16-trimethyl-15α(or β)-hydroxyprost-13(trans)-enoate (I)

1.5 g of methyl 9-ethylenedioxy-11α,16,16-trimethyl-15-hydroxyprost-13(trans)-enoate was dissolved in 50 ml of acetone and to the solution was added 12 ml of 7% hydrochloric acid at temperatures ranging from 3° to 5° C, followed by stirring for one hour. The mixture was diluted with 150 ml of a saturated aqueous sodium chloride solution and extracted three times with 100 ml of ethyl acetate each time. The extracts were washed with water, dried over anhydrous sodium sulfate and evaporated to dryness under reduced pressure to give 1.40 g of an oil which was subjected to thin layer chromatography using silica gel and developed with a mixture of ethyl acetate and n-hexane (1:3). There were obtained 0.28 g of methyl 9-oxo-11α,16,16-trimethyl-15α-hydroxy-prost-13(trans)-enoate from the portion of R$_f$ value around 0.3 and 0.56 g of methyl 9-oxo-11α,16,16-trimethyl-15β-hydroxyprost-13(trans)-enoate from the portion of R$_f$ value around 0.4.

Methyl 9-oxo-11α,16,16-trimethyl-15α-hydroxyprost-13(trans)-enoate

I.R. (liquid film) $\nu_{max}^{cm^{-1}}$:
  3500, 1735, 1200, 1170, 970
N.M.R. (CDCl$_3$) δ : ppm
  3.58 (3H, singlet, —COOC$\underline{H}_3$)
  3.75 (1H, doublet, 
                    |
                    OH 5.50 (2H, multiplet, $\underline{H}$
Mass spectrum M$^+$ : 394 (C$_{24}$H$_{42}$O$_4$)

Methyl 9-oxo-11α,16,16-trimethyl-15β-hydroxyprost-13(trans)-enoate

I.R. (liquid film) $\nu_{max}^{cm^{-1}}$:
  3500, 1740, 1200, 1170, 970
N.M.R. (CDCl$_3$) δ : ppm
  3.60 (3H, singlet, —COOC$\underline{H}_3$)
  3.80 (1H, doublet,
                    |
                    OH 5.50 (2H, multiplet, $\underline{H}$
Mass spectrum M$^+$ : 394 (C$_{24}$H$_{42}$O$_4$)

EXAMPLE 2

9-oxo-11α,16,16-trimethyl-15α-hydroxyprost-13(trans)-enoic acid 0.23 g of methyl 9-oxo-11α,16,16-trimethyl-15α-hydroxyprost-13(trans)-enoate was dissolved in 5 ml of methanol and to the solution was added 2.2 ml of 5% aqueous sodium hydroxide under ice-cooling, followed by stirring at room temperature for one hour. The reaction mixture was diluted with 100 ml of ice water, made weakly acidic by addition of dilute hydrochloric acid and saturated with sodium chloride. The mixture was extracted with ethyl acetate. The extract was washed with a saturated aqueous sodium chloride, dried over anhydrous sodium sulfate and evaporated to dryness under reduced pressure to afford 0.23 g of an oil which was purified by column chromatography using 3 g of silica gel to give 0.21 g of the desired product as oil.

I.R. (liquid film) $\nu_{max}^{cm^{-1}}$:
  3450, 3150, 2700, 1740, 1710, 1470, 1170, 970
N.M.R. (CDCl$_3$) δ: ppm
  3.87 (1H, doublet, 
                     |
                     OH
  5.05 (2H, multiplet, —COO$\underline{H}$ and —O$\underline{H}$)

5.62 (2H, multiplet, 
Mass spectrum M$^+$ : 380 (C$_{23}$H$_{40}$O$_4$)

EXAMPLE 3

9-oxo-11α,16,16-trimethyl-15β-hydroxyprost-13(trans)-enoic acid 0.53 g of methyl 9-oxo-11α,16,16-trimethyl-15β-hydroxyprost-13(trans)-enoate was dissolved in 10 ml of methanol and to the solution was added 3.4 ml of 5% aqueous sodium hydroxide under ice-cooling, followed by stirring at room temperature for one hour. The reaction mixture was diluted with 100 ml of ice water, made weakly acidic by addition of dilute hydrochloric acid and saturated with sodium chloride. The mixture was extracted with ethyl acetate. The extract was washed with a saturated aqueous sodium chloride, dried over anhydrous sodium sulfate and evaporated to dryness under reduced pressure to give 0.53 g of an oil which was purified by column chromatography using 6 g of silica gel to afford 0.51 g of the desired product as oil.

I.R. (liquid film) $\nu_{max}^{cm^{-1}}$:
 3450, 2650, 1740, 1710, 1470, 1250, 1165, 970
N.M.R. (CDCl$_3$) δ : ppm
 3.85 (1H, doublet, 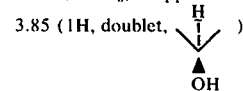 )
 5.43 (2H, multiplet, —COOH and —OH)
 5.58 (2H, multiplet, 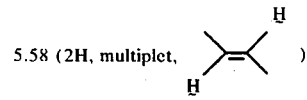 )
Mass spectrum M $^+$ : 380 (C$_{23}$H$_{40}$O$_4$)

EXAMPLE 4

Potassium 9-oxo-11α,16,16-trimethyl-15α-hydroxyprost-13(trans)-enoate 378 mg of 9-oxo-11α,16,16-trimethyl-15α-hydroxyprost-13(trans)-enoic acid was dissolved in 8 ml of 30% aqueous methanol and to the solution was added 10 ml of 30% aqueous methanol containing 100 mg of potassium hydrogencarbonate, followed by stirring at room temperature for one hour. After completion of the reaction, the solvent was distilled off under reduced pressure to give 463 mg of the desired product.

I.R. (liquid film) $\nu_{max}^{cm^{-1}}$ : 1593

EXAMPLE 5

Methyl 9oxo-11α-methyl-15ξ-hydroxyprost-13(trans)-enoate (I)

1. Methyl 9-ethylenedioxy-11α-methyl-15ξ-hydroxyprost-13(trans)-enoate (III)
 3.6 g of methyl 9-ethylenedioxy-11α-methyl-15-oxoprost-13(trans)-enoate was dissolved in 110 ml of absolute methanol. To the solution was added 0.33 g of sodium boron hydride in argon atmosphere at temperatures ranging from 3° to 5° C, followed by stirring for one hour. The reaction mixture was diluted with 200 ml of ice water containing 1 ml of glacial acetic acid and saturated with sodium chloride. The mixture was extracted three times with 100 ml of ethyl acetate each time. The extracts were washed with water, dried over anhydrous sodium sulfate and evaporated to dryness to give 3.6 g of oil which was purified by column chromatography using 110 g of silica gel to afford 3.3 g of the desired product as oil.

I.R. (liquid film) $\nu_{max}^{cm^{-1}}$ :
 3470, 1740, 1200, 1170, 1030, 970
N.M.R. (CDCl$_3$) δ : ppm
 0.90 (3H, doublet, —CH$_3$)
 3.64 (3H, singlet, —COOCH$_3$)
 3.86 (4H, broad singlet, 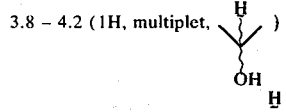)
 3.8 – 4.2 (1H, multiplet,  )
 5.43 (2H, multiplet,  )

2. Methyl 9-oxo-11α-methyl-15ξ-hydroxyprost-13(trans)-enoate (I)
 3.3 g of methyl 9-ethylenedioxy-11α-methyl-15ξ-hydroxyprost-13(trans)-enoate was dissolved in 100 ml of acetone and to the solution was added 25 ml of 7% aqueous hydrochloric acid at temperatures ranging from 3° to 5° C, followed by stirring for 1 hour. The mixture was diluted with 300 ml of a saturated aqueous sodium chloride and extracted three times with 100 ml of ethyl acetate each time. The extracts were washed with water, dried over anhydrous sodium sulfate and evaporated to dryness under reduced pressure to give 3.0 g of oil which was purified by column chromatography using 100 g of silica get to afford 2.85 g of the desired product as oil.

I.R. (liquid film) $\nu_{max}^{cm^{-1}}$ :
 3470, 1740, 1200, 1170, 975
N.M.R. (CDCl$_3$) δ : ppm
 3.63 (3H, singlet, —COOCH$_3$)
 4.10 (1H, multiplet,  )
 5.52 (2H, multiplet, 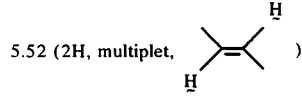 )

EXAMPLE 6

9-oxo-11α-methyl-15α(or β)-hydroxyprost-13(trans)-enoic acid (I)

2.77 g of methyl 9-oxo-11α-methyl-15ξ-hydroxyprost-13(trans)-enoate was dissolved in 55 ml of methanol. To the solution was added 22 ml of 5% aqueous sodium hydroxide under ice-cooling, followed by stirring at room temperature for one hour. The reaction mixture was diluted with 300 ml of ice water, made weakly acidic by addition of dilute aqueous hydrochloric acid and saturated with sodium chloride. The mixture was extracted three times with 100 ml of ethyl acetate each time. The extracts were washed with a saturated aqueous sodium chloride, dried over anhydrous sodium sulfate and evaporated to dryness under reduced pressure to give 2.75 g of crystaline residue which was recrystallized from a mixture of ethyl acetate and n-hexane to afford 1.06 g. of 9-oxo-11α-methyl-15α-hydroxyprost-13(trans)-enoic acid. The mother liquor was evaporated to 1.50 g of 9-oxo-11α-methyl-15β-hydroxyprost-13(trans)-enoic acid as oil which was crystallized by allowing to stand in a refrigerator. The crystal was recrystallized from a mixture of ethyl acetate and n-hexane to yield crystal of the 15β-hydroxyprostanoic acid melting at 40°–42° C.

9-oxo-11α-methyl-15α-hydroxyprost-13(trans)-enoic acid

I.R. (KBr) $\nu_{max}^{cm^{-1}}$ :
  3350, 2700, 1720, 1183, 980
N.M.R. (CD$_3$COCD$_3$) δ : ppm
  0.90 (3H, triplet, —CH$_2$CH$_3$)
  1.09 (3H, doublet, —CH$_3$)
  4.10 (1H, multiplet, 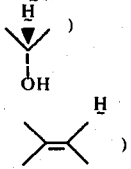 )
  5.59 (2H, multiplet,  )
Mass spectrum M$^+$ : 352 (C$_{21}$H$_{26}$O$_4$)
Elemental analysis:
  Calcd. for C$_{21}$H$_{36}$O$_4$ : C, 71.55; H, 10.30
  Found : C, 71.36; H, 10.25

9-oxo-11α-methyl-15β-hydroxyprost-13(trans)-enoic acid

I.R. (KBr) $\nu_{max}^{cm^{-1}}$ :
  3400, 3050, 1730, 1720, 1165
N.M.R. (CDCl$_3$) δ : ppm
  0.90 (3H, triplet, —CH$_2$CH$_3$)
  1.05 (3H, doublet, —CH$_3$)
  4.10 (1H, multiplet, 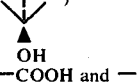 )
  4.40 (2H, mutiplet, —COOH and —OH)
  5.50 (2H, multiplet, 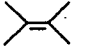 )
Mass spectrum M$^+$ : 352 (C$_{21}$H$_{36}$O$_4$)

EXAMPLE 7

Potassium 9-oxo-11α-methyl-15α-hydroxyprost-13(trans)-enoate (I)

352 mg of 9-oxo-11α-methyl-15α-hydroxyprost-13(trans)-enoic acid was dissolved in a mixture of 9 ml of methanol and 3 ml of water and to the solution was added 70 mg of potassium carbonate. The mixture was stirred at room temperature for 1 hour and evaporated to dryness under reduced pressure to give 395 mg of the desired product as powder.

I.R. (liquid paraffin) $\nu_{max}^{cm^{-1}}$ :
  3400, 1735, 1585 – 1560

EXAMPLE 8

Methyl 9-oxo-11α-methyl-15ξ-hydroxy-20-ethylprost-13(trans)-enoate (I)

1. Methyl 9-ethylenedioxy-11α-methyl-15ξ-hydroxy-20-ethylprost-13(trans)-enoate (III)

2.79 g of methyl 9-ethylenedioxy-11α-methyl-15-oxo-20-ethylprost-13(trans)-enoate was dissolved in 90 ml of absolute methanol and to the solution was added 0.25 g of sodium boron hydride in argon atmosphere at temperatures ranging from 3° to 5° C, followed by stirring for one hour. The reaction mixture was diluted with 300 ml of ice water containing 1 ml of glacial acetic acid and saturated with sodium chloride. The mixture was extracted with ethyl acetate. The extract was washed with water, dried over anhydrous sodium sulfate and evaporated to dryness under reduced pressure to give 3.0 g of oil which was purified by column chromatography using 30 g of silica gel to afford 2.54 g of the desired product as oil.

I.R. (liquid film) $\nu_{max}^{cm^{-1}}$ :
  3480, 1740, 1200, 1170, 970
N.M.R. (CDCl$_3$) δ : ppm
  3.67 (3H, singlet, —COOCH$_3$)
  3.90 (4H, singlet, 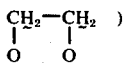 )
  4.08 (1H, multiplet,  )
  5.47 (2H, multiplet, 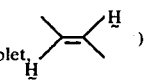 )

2. Methyl 9-oxo-11α-methyl-15α(or β)-hydroxy-20-ethylprost-13(trans)-enoate (I)

2.49 g of methyl 9-ethylenedioxy-11α-methyl-15ξ-hydroxy-20-ethylprost-13(trans)-enoate was dissolved in 80 ml of acetone and to the solution was added 20 ml of 7% aqueous hydrochloric acid at temperatures ranging from 3° to 5° C, followed by stirring for one hour. The reaction mixture was diluted with 250 ml of a saturated aqueous sodium chloride and extracted with ethyl acetate. The extract was washed with water, dried over anhydrous sodium sulfate and evaporated to dryness under reduced pressure to give 2.21 g of oil which was subjected to thin layer chromatography using silica gel and developed with a mixture of ethyl acetate and n-hexane (1:3). There were obtained 0.51 g of methyl 9-oxo-11α-methyl-15α-hydroxy-20-ethylprost-13(trans)-enoate from the portion of R$_f$ value around 0.3 and 0.85 g of methyl 9-oxo-11α-methyl-15β-hydroxy-20-ethylprost-13(trans)-enoate from the portion of R$_f$ value around 0.4.

Methyl 9-oxo-11α-methyl-15α-hydroxy-20-ethylprost-13(trans)-enoate

I.R. (liquid film) $\nu_{max}^{cm^{-1}}$:
    3500, 1740, 1200, 1170, 970
N.M.R. (CDCl$_3$) δ : ppm
    0.86 (3H, triplet, —CH$_2$CH$_3$)
    1.07 (3H, doublet, —CH$_3$)
    3.68 (3H, singlet, —COOCH$_3$)
    4.10 (1H, multiplet, 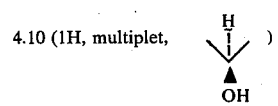 )

5.55 (2H, multiplet, 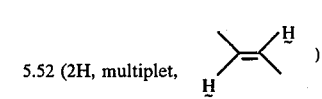 )

Mass spectrum M$^+$ : 394 (C$_{24}$H$_{42}$O$_4$)

Methyl 9-oxo-11α-methyl-15β-hydroxy-20-ethylprost-13(trans)-enoate

I.R. (liquid film) $\nu_{max}^{-1}$:
    3500, 1740, 1200, 1170, 970
N.M.R. (CDCl$_3$) δ : ppm
    0.86 (3H, triplet, —CH$_2$CH$_3$)

1.06 (3H, doublet, —CH$_3$)

3.68 (3H, singlet, 4.10 (1H, multiplet, 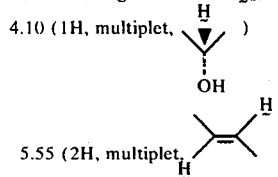 )

5.52 (2H, multiplet, 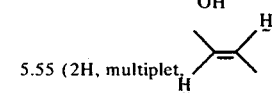 )

Mass spectrum M $^+$ : 394 (C$_{24}$H$_{42}$O$_4$)

EXAMPLE 9

9-oxo-11α-methyl-15α(or β)-hydroxy-20-ethylprost-13(trans)-enoic acid (I)

1. 0.50 g of methyl 9-oxo-11α-methyl-15α-hydroxy-20-ethylprost-13(trans)-enoate was dissolved in 10 ml of methanol and to the solution was added 4.4 ml of 5% aqueous sodium hydroxide at temperatures ranging from 3° to 5° C, followed by stirring at room temperature for one hour. The reaction mixture was diluted with 150 ml of ice water, made weakly acidic by addition of dilute hydrochloric acid and saturated with sodium chloride. The mixture was extracted with ethyl acetate. The extract was washed with a saturated aqueous sodium chloride, dried over anhydrous sodium sulfate and evaporated to dryness under reduced pressure to give 0.49 g of oil which was recrystallized from a mixture of ethyl acetate and n-hexane to afford 0.30 g of the desired product.

I.R. (liquid paraffin) $\nu_{max}^{cm^{-1}}$:
    3470, 1740, 1710, 1200, 970
N.M.R. (CDCl$_3$) δ : ppm
    0.87 (3H, triplet, —CH$_2$CH$_3$)
    1.10 (3H, doublet, —CH$_3$)

4.10 (1H, singlet, 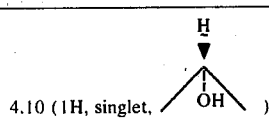 )

5.17 (2H, multiplet, —COOH and —OH)

5.48 (2H, multiplet, 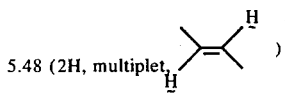 )

Mass spectrum M$^+$ : 380 (C$_{23}$H$_{40}$O$_4$)
Elemental analysis:
    Calcd. for C$_{23}$H$_{40}$O$_4$: C, 72.59; H, 10.60
    Found : C, 72.54; H, 10.60

EXAMPLE 10

9-oxo-11α-methyl-15β-hydroxy-20-ethylprost-13(trans)-enoic acid 0.80 g. of methyl 9-oxo-11α-methyl-15β-hydroxy-20-ethylprost-13(trans)-enoate was dissolved in 16 ml of methanol and to the solution was added 7 ml of 5% aqueous sodium hydroxide at temperatures ranging from 3° to 5° C, followed by stirring at room temperature for 1 hour. The reaction mixture was diluted with 200 ml of ice water, made weakly acidic and saturated with sodium chloride. The mixture was extracted with ethyl acetate. The extract was washed with a saturated aqueous sodium chloride, dried over anhydrous sodium sulfate and evaporated to dryness under reduced pressure to give 0.75 g of the desired product as oil.

I.R. (liquid film) $\nu_{max}^{cm^{-1}}$:
    3400, 3050, 2700, 1740, 1720, 1170
N.M.R. (CDCl$_3$) δ : ppm
    0.88 (3H, triplet, —CH$_2$CH$_3$)

1.08 (3H, doublet, —CH$_3$)

4.10 (1H, singlet, 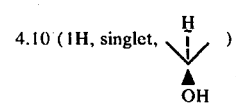 )

5.35 (2H, multiplet, —COOH and —OH)

5.50 (2H, multiplet, 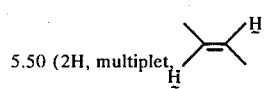 )

Mass spectrum M$^+$ : 380 (C$_{23}$H$_{40}$O$_4$)

What is claimed is:
1. Prostanoic acid derivatives having the formula

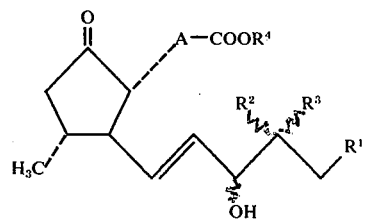

wherein A is hexamethylene, R$^1$ is n-propyl, R$^2$ and R$^3$ may be the same or different and each represents an alkyl group having from one to 4 carbon atoms, and R$^4$ represents hydrogen atom or an alkyl group having from one to 4 carbon atoms, and the pharmaceutically acceptable salts thereof.

2. 9-oxo-11α,16,16-trimethyl-15α(or β)-hydroxyprost-13(trans)-enoic acid.

3. Methyl 9-oxo-11α,16,16-trimethyl-15α(or β)-hydroxyprost-13(trans)-enoate.

4. Potassium 9-oxo-11α,16,16-trimethyl-15α(or β)-hydroxyprost-13(trans)-enoate.

* * * * *

UNITED STATES PATENT OFFICE
CERTIFICATE OF CORRECTION

Patent No. 3,996,263          Dated December 7, 1976

Inventor(s) Kiyoshi Sakai et al

It is certified that error appears in the above-identified patent and that said Letters Patent are hereby corrected as shown below:

Title page and Column 1, title: rewrite "PREPARAION"
     as --- PREPARATION ---.

Column 6, line 64: after "as", delete "a".

Column 11, line 8: replace "260-methoxycarbonyl" with
     --- 2β-methoxycarbonyl ---.

Column 14, before line 20: insert the following
     --- Elemental analysis    Calcd. for $C_8H_{10}O_3$:
     C, 62.32; H, 6.54    Found: C, 62.27; H, 6.43 ---.

Column 14, before line 60: insert the following
     --- Elemental analysis    Calcd. for $C_{16}H_{24}O_5$:
     C, 64.84; H, 8.16    Found: C, 64.87; H, 8.34 ---.

Column 16, line 48: replace "Methy" with --- Methyl ---.

UNITED STATES PATENT OFFICE
CERTIFICATE OF CORRECTION

Patent No. 3,996,263  Dated December 7, 1976

Inventor(s) Kiyoshi Sakai et al

It is certified that error appears in the above-identified patent and that said Letters Patent are hereby corrected as shown below:

Column 23, line 27: after "Mass spectrum $M^+$:, replace "352($C_{21}H_{26}O_4$)" with --- 352($C_{21}H_{36}O_4$) ---.

Column 25, line 31: after "(3H, singlet,", insert --- -COO$\underline{CH}_3$) ---.

Signed and Sealed this

Twentieth Day of September 1977

[SEAL]

Attest:

RUTH C. MASON  
Attesting Officer

LUTRELLE F. PARKER  
Acting Commissioner of Patents and Trademarks